United States Patent [19]

Roy

[11] Patent Number: Plant 7,288

[45] Date of Patent: Aug. 7, 1990

[54] ROSE PLANT — ROYPINPRO VARIETY

[75] Inventor: Elysee Roy, Deols, France

[73] Assignee: The Conard-Pyle Company, West Grove, Pa.

[21] Appl. No.: 349,857

[22] Filed: May 10, 1989

[51] Int. Cl.[5] ..... A01H 5/00

[52] U.S. Cl. ..... Plt./18

[58] Field of Search ..... Plt. 17, 18

[56] References Cited

U.S. PATENT DOCUMENTS

P.P. 4,017 2/1977 Royon ..... Plt. 18

*Primary Examiner*—James R. Feyrer

*Attorney, Agent, or Firm*—Burns, Doane, Swecker & Mathis

[57] ABSTRACT

A new and distinct variety of Grandiflora rose plant is provided which forms in abundance attractive long lasting double blossoms which are light salmon pink in coloration. The plant exhibits an upright growth habit, forms vigorous vegetation, and is well suited for cut flower production. The blossoms exhibit a pronounced fruity fragrance. Good resistance to diseases is manifest.

1 Drawing Sheet

SUMMARY OF THE INVENTION

The new variety of Grandiflora rose plant of the present invention is a spontaneous sport of the SONIA variety (U.S. Plant Pat. No. 3,095) of unknown causation. The discovery of such sport occurred during the selective study of many plants resulting from the grafting of buds obtained from the Sonia variety. The Sonia variety sometimes has been known as the Sweet Promise variety.

The characteristics of the new variety are substantially similar to those of the Sonia variety with the primary exception that the blossoms of the new variety are light salmon pink in coloration instead of porcelain rose touched with begonia pink. Otherwise the blossom configuration is substantially the same as that of the SONIA variety.

It was found that the new variety of Grandiflora rose plant of the present invention possesses the following combination of characteristics:

(a) forms in abundance attractive long lasting blossoms which are light salmon pink in coloration and which exhibit a pronounced fruity fragrance,
(b) exhibits an upright growth habit which is well suited for cut flower production,
(c) forms vigorous vegetation, and
(d) exhibits good resistance to disease.

The new variety well meets the needs of the horticultural for all uses. It is particularly well-suited for the production of cut flowers. Alternatively, it may form attractive ornamentation in parks and gardens.

The new variety has been found to undergo asexual propagation by a number of routes, including budding, grafting, cuttage, etc. The characteristics of the new variety have been found to be stable and strictly transmissible by such asexual propagation from one generation to another.

The new variety has been named the Roypinpro variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and observed during February while budded on *Rosa indicia* understock and growing in a greenhouse at Cap d'Antibes, France.

FIG. 7 illustrates a specimen of a fully open flower — plan view — reverse;

FIG. 13 illustrates a specimen of a main branch;

DETAILED DESCRIPTION

Figures 1, 2, 3, 4, 5, 6, 8, 9, 10, 11, 12, 14, 15, 16, 17:
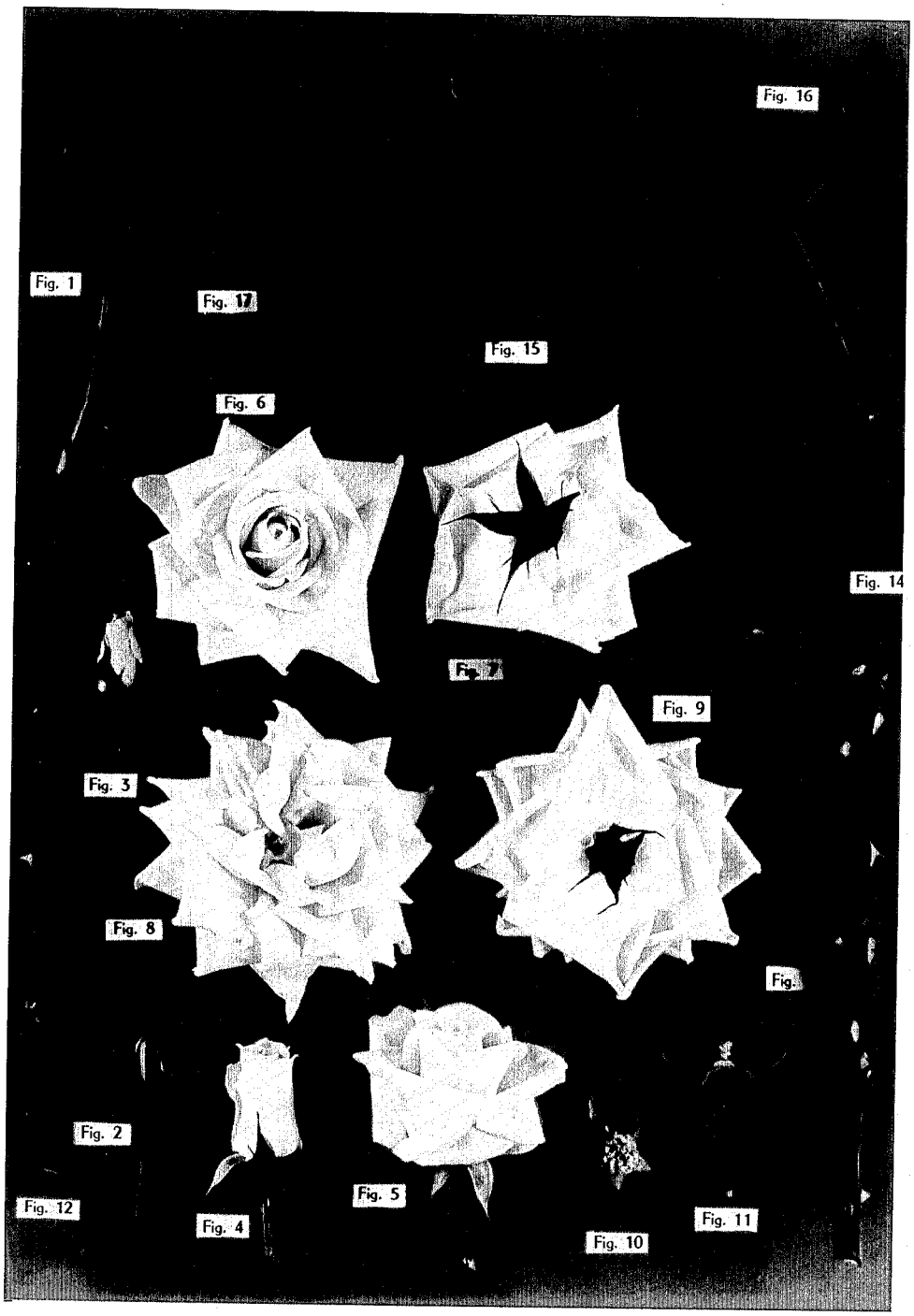
FIG. 1 illustrates a specimen of a young shoot.
FIG. 2 illustrates a specimen of a floral bud before the opening of the sepals.
FIG. 3 illustrates a specimen of a floral bud when the sepals open and before the petals open.
FIG. 4 illustrates a specimen of a floral bud when the petals open.
FIG. 5 illustrates a specimen of a flower in the course of opening.
FIG. 6 illustrates a specimen of a fully open flower — plan view — obverse.
FIG. 8 illustrates a specimen of a fully open flower immediately prior to petal drop — plan view — obverse.
FIG. 9 illustrates a specimen of a fully open flower immediately prior to petal drop — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 14 illustrates a specimen of a leaf with three leaflets — plan view — upper surface.
FIG. 15 illustrates a specimen of a leaf with five leaflets — plan view — upper surface.
FIG. 16 illustrates a specimen of a leaf with seven leaflets — plan view — under surface.
FIG. 17 illustrates a specimen of a leaf with nine leaflets — plan view — upper surface.

The chart used in the identification of the colors is that of The Royal Horticultural Society (R.H.S. Colour Chart). The description is based on observations of two year old specimens made during February while budded on *Rosa indica* understock and growing in a greenhouse at Cap d'Antibes, France. Color terminology in common terms precedes the reference to such chart.

Class: Grandiflora.

Plant:

*Height.*—Plants which are pruned to a height of 85 cm. commonly produce floral stems having a length of approximately 40 to 70 cm.

*Habit.*—Upright.

Branches:

*Color.*—Young stems: lettuce green, Yellow-Green Group 144A, more or less stained reddish brown. Adult wood: light green, Yellow-Green Group 146B.

*Thorns.*—Size: medium. Quantity: average and frequently mixed with needle-shaped bristles. Color: reddish on young stems and greenish pink on adult wood which changes to straw and eventually to tan.

Leaves:

*Stipules.*—Adnate, pectinate, commonly rather narrow and poorly developed.

Petioles.—Upper surface: striped, reddish brown on young foliage and medium green on adult wood. Under surface: light green, bear some small hooked thorns.

Leaflets.—Numer: 3, 5, 7, and sometimes 9. Shape: elliptical with more or less acuminate tips. Serration: simple and rather regular. Texture: leathery. General appearance: dull and rather dense with large foliage. Color (young foliage): Upper surface: lettuce green, Yellow-Green Group 144A, more or less stained with reddish coloration. Under surface: lettuce green, Yellow-Green Group 144B, more or less stained with reddish coloration. Color (adult foliage): Upper surface: dark green, Yellow-Green Group 147A. Under surface: medium green, Yellow-Green Group 147B.

Inflorescence:

*Number of flowers.*—Generally one per stem.

*Peduncle.*—Straight, rigid, bears a few tiny prickles mixed with small pediculate glands, approximately 7 to 10 cm. in length on average.

Sepals.—Upper surface: tomentose, and greenish in coloration. Under surface: light green in coloration, smooth and relatively narrow.

*Buds.*—Shape: elongated and somewhat cylindrical. Length: approximately 3.5 cm. on average. Size: medium. Color when opening: Upper surface: medium salmon pink, Orange Group 27A, and turning white at the edges of the petals. Under surface: very light pink, Orange Group 27D.

Flower.—Shape: double, initially elongated with a high center and upon the passage of time assume the configuration of a hollow cup. Diameter: approximately 10 to 12 cm. on average. Color (when opening begins): Upper surface: medium salmon pink, Orange Group 27A, and turning white at the edges of the petals. Under surface; very light pink, Orange Group 27D. Color (when blooming): Upper surface: light salmon pink, Orange Group 27C. Under surface: very light pink, Orange Group 27D. Color (at end of opening): Upper surface: salmon pink, Orange Group 27C. Under surface: very light pink, Orange Group 27D. Fragrance: strong and fruity. Lasting quality: long lasting on plant and when cut and present in a vase. Petal number: approximately 25 to 30 on average. Petal form: widely rounded and folding into a point when open, the inner petals close to the stamens are not always fully developed and often exhibit a central whitish vein together with fairly well defined indentations.

*Texture.*—Very consistent. petal drop: they drop off cleanly. stamen number: approximately 110 on average. anthers: normal and yellowish in coloration. filaments: evenly disposed around the receptacle, the longer ones tend to be yellowish in coloration and the others tend to be pinkish in coloration. pistils: approximately 70 on average. stigmas: normal, yellowish in coloration. styles: more or less restricted and twisted, commonly yellowish at the base and fuschia red near the stigma. receptacle: light green in coloration, smooth, and in longitudinal section it is in the shape of a pitcher.

Development:

*Vegetation.*—Very vigorous.

*Blooming.*—Very abundant.

*Aptitude to forcing.*—Excellent.

*Resistance to diseases.*—Very good.

I claim:

1. A new and distinct variety of Grandiflora rose plant characterized by the following combination of characteristics:

(a) forms in abundance attractive long lasting blossoms which are light salmon pink in coloration and which exhibit a pronounced fruity fragrance,
(b) exhibits an upright growth habit which is well suited for cut flower production,
(c) forms vigorous vegetation, and
(d) exhibits good resistance to diseases;

substantially as herein shown and described.

* * * * *